US00PP26092P3

(12) United States Plant Patent
Danziger

(10) Patent No.: US PP26,092 P3
(45) Date of Patent: Nov. 17, 2015

(54) ***LOBULARIA* PLANT NAMED 'DLOBU23'**

(50) Latin Name: *Lobularia maritima*
Varietal Denomination: DLOBU23

(71) Applicant: Gavriel Danziger, Moshav Mishmar Hashiva (IL)

(72) Inventor: Gavriel Danziger, Moshav Mishmar Hashiva (IL)

(73) Assignee: Danziger "DAN" Flower Farm (IL)

( * ) Notice: Subject to any disclaimer, the term of this patent is extended or adjusted under 35 U.S.C. 154(b) by 105 days.

(21) Appl. No.: 13/999,044

(22) Filed: Jan. 6, 2014

(65) Prior Publication Data

US 2015/0195982 P1 Jul. 9, 2015

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Cassandra Bright

(57) ABSTRACT

A new and distinct *Lobularia* cultivar named 'DLOBU23' is disclosed, characterized by fragrant, long lasting flowers. The new variety produces a compact, free-branching, dense, semi-trailing plant, long lasting flowers and dark purple flowers. The new variety is a *Lobularia,* normally produced as an outdoor garden or container plant.

2 Drawing Sheets

Latin name of the genus and species: *Lobularia maritima.*
Variety denomination: 'DLOBU23'.

BACKGROUND OF THE INVENTION

The new *Lobularia* cultivar is a product of a planned breeding program conducted by the inventor, Gavriel Danziger, in Moshav Mishmar Hashiva, Israel. The objective of the breeding program was to produce new *Lobularia* varieties for ornamental commercial applications. The open polination resulting in this new variety was made during February of 2011.

The seed parent is the unpatented, proprietary seedling variety referred to as *Lobularia maritima* 'AY-10-184' The pollen parent is unknown as it was an open pollination breeding program. The new variety was discovered in February of 2012 by the inventor in a group of seedlings resulting from the 2011 open pollination, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel during February of 2012 and has shown that the unique features of this cultivar are stable and reproduced true to type through many generations.

SUMMARY OF THE INVENTION

The cultivar 'DLOBU23' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DLOBU23' These characteristics in combination distinguish 'DLOBU23' as a new and distinct *Lobularia* cultivar:

1. Semi-trailing, compact and dense plant habit.
2. Long lasting flowers.

3. Freely branching.
4. Dark purple flower color.

Plants of the new cultivar 'DLOBU23' are similar to plants of the seed parent, *Lobularia maritima* 'AY-10-184' in most horticultural characteristics, however, plants of the new cultivar 'DLOBU23' differ in the following:

1. Bushier plant form.
2. Greater floriferousness.
3. Flower of a darker purple color.
4. Better heat tolerance.

COMMERCIAL COMPARISON

Plants of the new cultivar 'DLOBU23' are comparable to the unpatented commercial variety *Lobularia* 'Alyssum Aphrodite Wine Red'. The two *Lobularia* varieties are similar in most horticultural characteristics; however, the new variety 'DLOBU23' differs in the following ways:

1. Dark purple flower; the comparator flowers are magenta colored.
2. Longer flowering period.
3. More trailing plant form.

Plants of the new cultivar 'DLOBU23' are also comparable to the unpatented commercial variety *Lobularia* 'Snow Princess'. The two *Lobularia* varieties are similar in most horticultural characteristics; however, the new variety 'DLOBU23' differs in the following ways:

1. More compact and less vigorous.
2. Smaller leaves.
3. Shorter and tighter inflorescence.
4. Not sterile, comparator is sterile.
5. Smaller flowers.

BRIEF DESCRIPTION OF THE PHOTOGRAPHS

Figure 1:
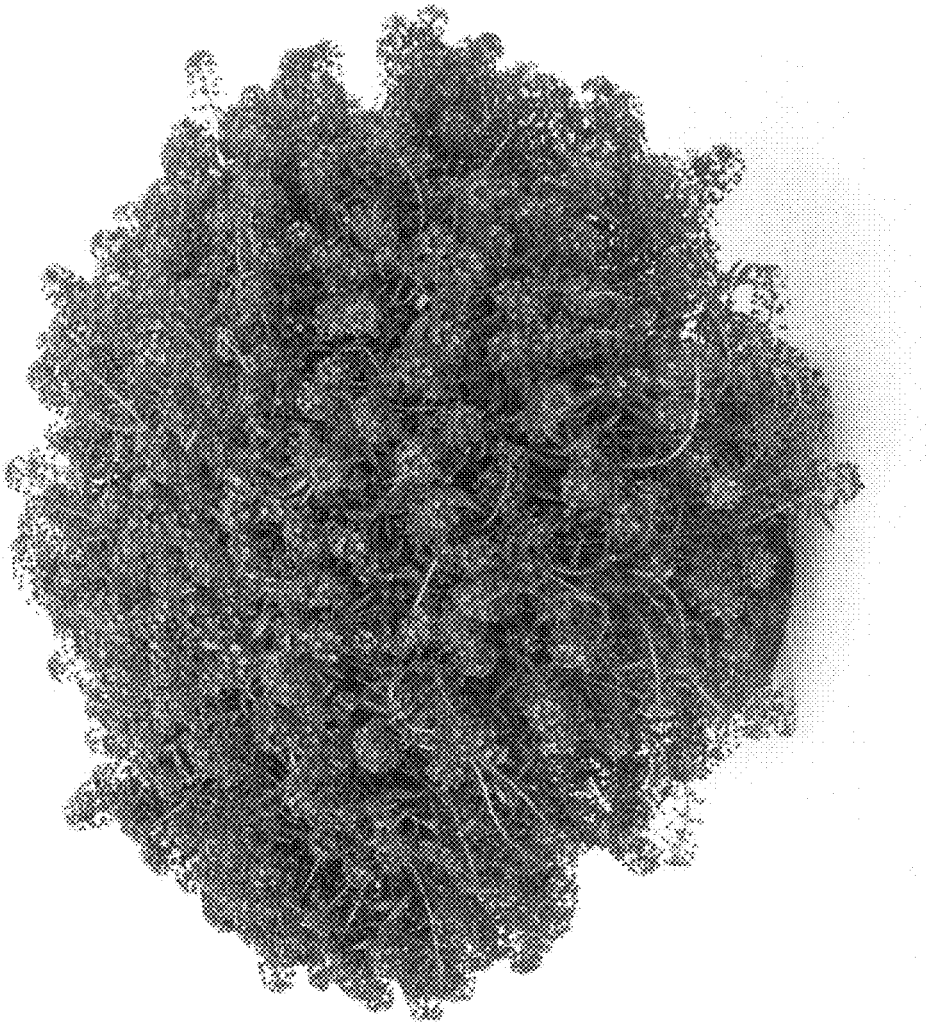

The accompanying photograph in FIG. 1 illustrates in full color a typical plant of 'DLOBU23' grown in a greenhouse, in a 13 cm pot. Age of the plant photographed is approximately 10 weeks from a sticking.

Figure 2:
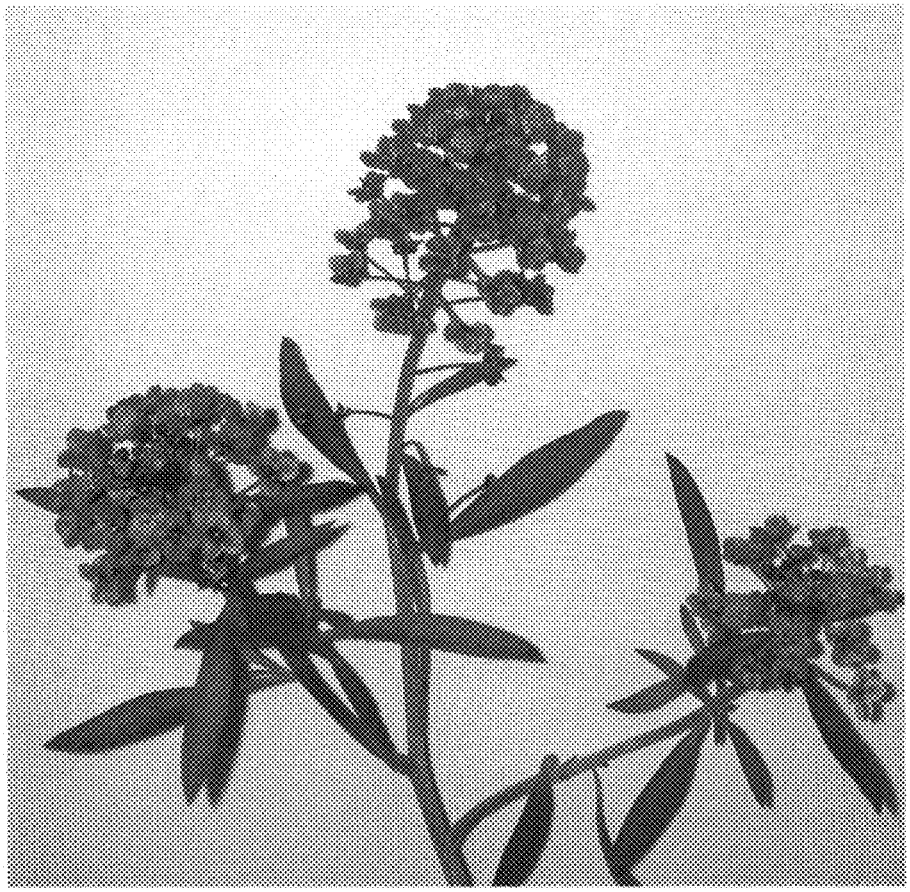

FIG. 2 illustrates in full color a close up of a typical bloom of 'DLOBU23'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DLOBU23' plants grown in a greenhouse during Autumn to Spring in Moshav Mishmar Hashiva, Israel. The growing temperature ranged from 18° C. to 30° C. during the day and from 9° C. to 16° C. during the night. General light conditions are high light levels of 60,000 to 90,000 lux. Measurements and numerical values represent averages of typical plant types.

Botanical classification: *Lobularia maritima* 'DLOBU23'.

PROPAGATION

Typical propagation material: Cuttings.
Time to rooting: 14 to 21 days at approximately 16° C.
Root description: Thin, fibrous, freely branching, near White RHS 155C in color.

PLANT

Age of plant described: Approximately 10 weeks.
Height: Approximately 9 cm.
Plant spread: Approximately 30 cm (radius).
Growth rate: Medium.
Branching characteristics: Freely Branching.
Approximate quantity of lateral branches: Approximately 5 primary lateral branches and numerous secondary and tertiary lateral branches.
Length of lateral branches: Approximately 25 cm.
Diameter of lateral branches: Approximately 0.3 cm.
Texture of lateral branches: Slightly Pubescent.
Lateral branch shape: Hexagonal in cross section.
Lateral branch strength: Strong.
Lateral branch color: Approximately Yellow-green RHS 144A.
Internode length: 2 cm (average).
Number of leaves per lateral branch: Average 24 (per branch).

FOLIAGE

Leaf:
- *Arrangement.*—Alternate.
- *Shape of blade.*—Oblanceolate.
- *Average length.*—Approximately 4-4.5 cm. (Mature foliage — 5-6 cm).
- *Average width.*—Approximately 0.5-0.8 cm. (Mature foliage — 1 cm).
- *Apex.*—Acute.
- *Base.*—Cuneate.
- *Attachment.*—Sessile.
- *Margin.*—Entire.
- *Texture of top surface.*—Slightly Pubescent.
- *Texture of bottom surface.*—Slightly Pubescent.
- *Color.*—Young foliage upper side: Near Green RHS 137A. Young foliage under side: Near Green RHS 137C. Mature foliage upper side: Near Green RHS 137B. Mature foliage under side: Near Green RHS 137C.
- *Venation.*—Indistinguishable from foliage.

Petiole: None.

FLOWER

Bloom period:
- *Natural season.*—Long lasting flowering period. From March through December.
- *In commercial production, flowering begins from a rooted cutting in.*—Approximately 7-8 weeks.

Inflorescence:
- *Arrangement.*—Panicle.
- *Height.*—Approximately 5-9 cm in 10 week old plant. (mature inflorescence can reach 15 cm).
- *Width.*—Approximately 2-3 cm.
- *Quantity of flowers per inflorescence.*—Approximately 60-70 (40 open flowers).

Bud:
- *Bud shape.*—Globose.
- *Bud length.*—Approximately 1.5 mm.
- *Bud diameter.*—Approximately 1.5 mm.
- *Bud color.*—Near Green group RHS 143A.
- *Rate of opening.*—Individual flowers fully open approximately 1-3 days from the bud stage.

Individual flower:
- *Shape.*—Cross shaped single flowers.
- *Quantity of flowers and buds per plant.*—Approximately 60-70 flowers and buds per inflorescence — more than 2500 flowers per plant.
- *Diameter of entire flower.*—Approximately 0.5-0.6 cm.
- *Depth of flower.*—Approximately 1 mm.
- *Flower longevity on plant.*—Approximately 6-7 days.
- *Persistent or self-cleaning.*—Self-cleaning.
- *Fragrance.*—Sweet, honey like.

Petals:
- *Length of petal.*—Approximately 2.5 mm.
- *Width of petal.*—Approximately 2 mm.
- *Apex.*—Rounded.
- *Base.*—Reniform.
- *Shape of petal.*—Oval.
- *Petal margin.*—Entire.
- *Petal arrangement.*—4 petals fused in a single whorl.
- *Petal number.*—4 petals.
- *Petal appearance.*—Matte.
- *Petal texture.*—Smooth, glabrous all surfaces.

Color:
- *Upper surface at first opening.*—Near Purple-violet RHS N81 B.
- *Upper surface at maturity.*—Near Purple-violet RHS N81 A.
- *Upper surface at fading.*—Near Purple-violet RHS N81 B.
- *Under surface at first opening.*—Near Purple-violet RHS N81 B.
- *Under surface at maturity.*—Near Purple-violet RHS N81 A.
- *Under surface at fading.*—Near Violet RHS 83 A (Dark purple at the end).

Petaloids or other floral structures: Not observed.

Sepal:
- *Number.*—4.
- *Sepal appearance.*—4 sepals.

*Sepal arrangement.*—4 sepals in a single whorl.
*Sepal length.*—Approximately 1 mm.
*Sepal width.*—Approximately 0.5 mm.
*Sepal shape.*—Elliptic.
*Base.*—Truncate.
*Apex shape.*—Acute.
*Margin.*—Entire.
*Color.*—Near Green RHS 143A all surfaces.

Peduncle:
*Length.*—Approximately 2-2.5 cm.
*Diameter.*—Approximately 2 mm.
*Color.*—Near Yellow-green RHS 144A.
*Strength.*—Strong.

Pedicel:
*Length.*—Approximately 1 cm.
*Diameter.*—Approximately 0.6 mm.
*Angle.*—Approximately 80-90 degrees.
*Strength.*—Flexible, moderately strong.
*Color.*—Near Yellow-green RHS 144A.

REPRODUCTIVE ORGANS

Number of pistils per flower: 1.
Pistil length: Approximately 1 mm.
Stigma shape: Rounded to broadly spreading.
Stigma color: Near Yellow-green RHS 144C.
Style color: Near Yellow-green RHS 144B.
Style length: Approximately 0.5 mm.
Ovary color: Near Yellow-green RHS 144C.
Stamens quantity: 6.
Stamen length: 1.5 mm.
Anther shape: Elliptic.
Anther size: 0.5 mm.
Anther color: Near Yellow RHS 7B.
Pollen color: Near Yellow RHS 7A.
Pollen quantity: Moderate.

OTHER CHARACTERISTICS

Disease and pest resistance: Neither resistance nor susceptibility to the normal diseases and pests of the species has been observed.

Drought tolerance and cold tolerance: Plants of the candidate variety have been noted to have good tolerance at temperatures from 1° C. to 38 ° C. and also tolerate rainy conditions.

Fruit/seed production: Color and Shape of Fruits and Seeds : The fruits and Seeds are elliptical and flat. The color of the mature seed is near Grey-purple RHS N187A.

What is claimed is:

1. A new and distinct cultivar of *Lobularia* plant named 'DLOBU23' as herein illustrated and described.

* * * * *